May 3, 1966 E. S. BOERNER Plant Pat. 2,629
ROSE PLANT
Filed Jan. 14, 1965
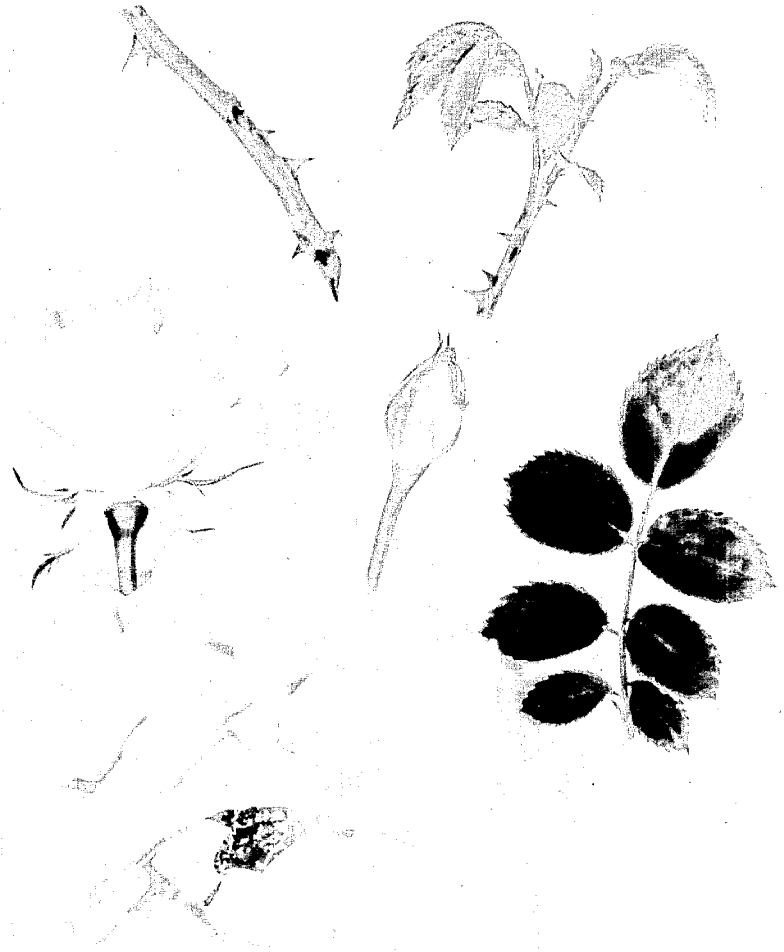
Inventor.
E. S. Boerner
By: Robb & Robb
Attorneys.

United States Patent Office

Plant Pat. 2,629
Patented May 3, 1966

2,629
ROSE PLANT

Eugene S. Boerner, Newark, N.Y., assignor to Jackson & Perkins Company, Newark, N.Y., a corporation of New York Filed Jan. 14, 1965, Ser. No. 425,651
1 Claim. (Cl. Plt.—18)

The present invention relates to a new and distinct variety of rose plant of the hybrid tea class, which was originated by me by crossing an unnamed and unpatented seedling of "Serenade" (Plant Patent No. 852) × "Fashion" (Plant Patent No. 789) with the variety "Golden Masterpiece" (Plant Patent No. 1,284).

The primary objective of this breeding was to produce a new and improved rose variety of the hybrid tea class which bears large high-centered flowers, and which has some of the influence of a floribunda rose to strengthen it. This objective was fully achieved, along with other desirable improvements, as evidenced by the following unique combination of characteristics which are outstanding in the new variety and which distinguish it from its parents, as well as from all other varieties of which I am aware:

(1) Long ovoid flower buds;

(2) A large open flower size, with the flowers being high-centered;

(3) A distinctive and attractive translucent flower color corresponding to Eosine Pink, with the reverse of the petals being La France Pink, very lightly overcast with Eosine Pink, and the petals being Buff-Yellow at the hinge; and (4) Long-lasting qualities of the flowers both in the garden and as cut flowers.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Serenade" × "Fashion."
*Pollen parent.*—"Golden Masterpiece."
Classification:
*Botanic.*—Hybrid tea.
*Commercial.*—Hybrid tea.

*Flower*

(Observations made from specimens grown outdoors at Newark, New York, in the early morning near the middle of August.)

Blooming habit: Recurrent—continuous.
Bud:
*Size.*—Large.
*Form.*—Long and ovoid; not affected by wet or hot weather.
*Color.*—When sepals first divide—Acajou Red, Plate 13. When petals begin to unfurl—Eugenia Red, Plate 13, with the lower half of petals overcast with Pale Greenish Yellow, Plate 5. When half-blown: Inside of petals—Begonia Rose, Plate 1, very lightly overcast with Geranium Pink, Plate 1; reverse of petals—Geranium Pink, Plate 1, lightly overcast with Orange-Pink, Plate 2 in the center of the petal.
*Sepals.*—Slightly branched; curl back when petals begin to unfurl. Color: Inside—Pale Lumiere Green, Plate 17; outside—Light Cress Green, Plate 31.
*Calyx.*—Color—Biscay Green, Plate 17. Shape—funnel. Size—small. Aspect—smooth. Odor when rubbed—none.
*Peduncle.*—Length—long. Aspect—rough. Strength—erect; slender. Color—Parrot Green, Plate 6.
*Opening.*—Opens up well; is not affected by adverse weather conditions.
Bloom:
*Size.*—Large. Average size when fully expanded—from 5½ inches to 6 inches.
*Borne.*—Both singly and several together.
*Stems.*—Long; strong.
*Form (when first open).*—High-centered. Permanence—retains its form to the end but outer petals curl back.
*Petalage.*—Double (full but open center). Number of petals under normal conditions—from 45 to 50.
*Color.*—Center of flower—Geranium Pink, Plate 1, very lightly overcast with Eosine Pink, Plate 1. Outer petals—Eosine Pink, Plate 1, overcast with La France Pink, Plate 1. Base of petals—Buff-Yellow, Plate 4. Inside of petals—Eosine Pink, Plate 1. Reverse of petals—La France Pink, Plate 1, very lightly overcast with Eosine Pink, Plate 1, with lower half of petals overcast with Buff-Yellow, Plate 4. General tonality from a distance—Eosine Pink, Plate 1, lightly overcast with Geranium Pink, Plate 1.
*Discoloration.*—General tonality at end of first day—Geranium Pink, Plate 1, very lightly overcast with Eosine Pink, Plate 1. Second day—Eosine Pink, Plate 1. Third day—Eosine Pink, Plate 1.
Petals:
*Texture.*—Thick; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Medium size; many; regularly arranged around styles. Color—Capucine Orange, Plate 3.
Stamens, filaments (threads): Long. Color—Rose Doree, Plate 1.
Pollen: Color—Pale Yellow-Orange, Plate 3.
Styles: Loosely separated; uneven length; short; thin.
Stigmans: Color—Flame Scarlet, Plate 2.
Ovaries: All enclosed in calyx.
Hips: None.
Seeds: None.

*Plant*

Form: Bush.
Growth: Vigorous; upright.
Foliage: Compound of 3 to 7 leaflets.
*Size.*—Large.
*Quantity.*—Normal.

*Color.*—New foliage: Upper side—Biscay Green, Plate 17; under side—Apple Green, Plate 17, overcast lightly with Eugenia Red, Plate 13. Old foliage: Upper side—Bice Green, Plate 17; under side—Courge Green, Plate 17.

*Shape.*—Oval pointed.

*Texture.*—Upper side—leathery; under side—smooth.

*Ribs and veins.*—Ordinary.

*Edge.*—Serrated (saw toothed).

*Serration.*—Both double and single; small.

*Leaf stem.*—Color—Yellowish Citrine, Plate 16. Under side—prickly.

*Stipules.*—Medium length; serrated.

Wood:

*New wood.*—Color—Yellowish Oil Green, Plate 5. Bark—smooth.

*Oil wood.*—Color—Light Bice Green, Plate 17. Bark—smooth.

Thorns:

*Thorns.*—Quantity: On main stalks from base—ordinary; on laterals from stalk—ordinary. Form—narrow base; medium length; some straight and some hooked downward. Color (when young)—Acajou Red, Plate 13. Position—irregular.

*Prickles.*—Quantity: On main stalks—none; on laterals—none.

*Short needles.*—Quantity: On main stalks—none; on laterals—none.

I claim:

A new and distinct variety of rose plant of the hybrid tea class, substantially as herein shown and described, characterized particularly as to novelty by the unique combination of long ovoid flower buds, a large open flower size, with the flowers being high-centered, a distinctive and attractive translucent flower color corresponding to Eosine Pink, with the reverse of the petals being La France Pink, very lightly overcast with Eosine Pink, and the petals being Buff-Yellow at the hinge, and long-lasting qualities of the flowers both in the garden and as cut flowers.

No references cited.

ANTONIO F. GUIDA, *Acting Primary Examiner.*